United States Patent
Bucala et al.

(10) Patent No.: US 6,774,227 B1
(45) Date of Patent: Aug. 10, 2004

(54) THERAPEUTIC USES OF FACTORS WHICH INHIBIT OR NEUTRALIZE MIF ACTIVITY

(75) Inventors: Richard J. Bucala, Cos Cob, CT (US); Jason Chesney, Minneapolis, MN (US)

(73) Assignee: Cytokine PharmaSciences, Inc., King of Prussia, PA (US)

( * ) Notice: Subject to any disclaimer, the term of this patent is extended or adjusted under 35 U.S.C. 154(b) by 0 days.

(21) Appl. No.: 08/738,947

(22) Filed: Oct. 24, 1996

Related U.S. Application Data

(63) Continuation-in-part of application No. 08/462,350, filed on Jun. 5, 1995, now abandoned, which is a continuation-in-part of application No. 08/243,342, filed on May 16, 1994, now abandoned, which is a continuation-in-part of application No. 08/063,399, filed on May 17, 1993, now abandoned.

(51) Int. Cl.[7] .......................... C07H 21/04; A61K 48/00
(52) U.S. Cl. .......................... 536/24.5; 536/23.1; 435/6
(58) Field of Search ............................. 514/44; 435/6; 536/23.1, 24.33, 24.5

(56) References Cited

U.S. PATENT DOCUMENTS 5,585,479 A * 12/1996 Hoke et al.

FOREIGN PATENT DOCUMENTS

WO    WO 90/11301    * 10/1990

OTHER PUBLICATIONS

Rojanasakul, Antisense oligonucleotide therapeutics: drug delivery and targeting, Advanced Drug Delivery Reviews, vol. 18, pp. 115–131, 1996.*
Gewirtz et al., Facilitating oligonucleotide delivery: Helping antisense deliver on its promise, Proc. Natl. Acad. Sci., vol. 93, pp. 3161–3163, Apr. 1998.*
Branch, A good antisense is hard to find, TIBS, vol. 23, pp. 45–50, Feb. 1998.*
Pozzi et al., Human recombinant migration inhibitory factor activates human macrophages to kill tumor cells, Cellular Immunology, vol. 145, pp. 372–379, 1992.*
Uhlmann et al., Antisense oligonucleotides: A new therapeutic principle, Chemical Reviews, vol. 90 (4), pp. 543–584, Jun. 1990.*

* cited by examiner

*Primary Examiner*—Andrew Wang
*Assistant Examiner*—James Douglas Schultz
(74) *Attorney, Agent, or Firm*—Steven B. Kelber; Piper Rudnick LLP

(57) ABSTRACT

The present invention relates to methods of treating disorders related to cellular overproliferation comprising neutralizing the production or activity of macrophage migration inhibitory factor (MIF). The invention also relates to therapeutic compositions comprising factors which inhibit or neutralize MIF activity, such as, MIF antisense RNA molecules and MIF monoclonal antibodies and derivatives or analogs thereof. The invention further relates to the uses of such compositions and methods for the treatment of malignancies, including, but not limited to, B and T cell lymphomas.

Figure 1:
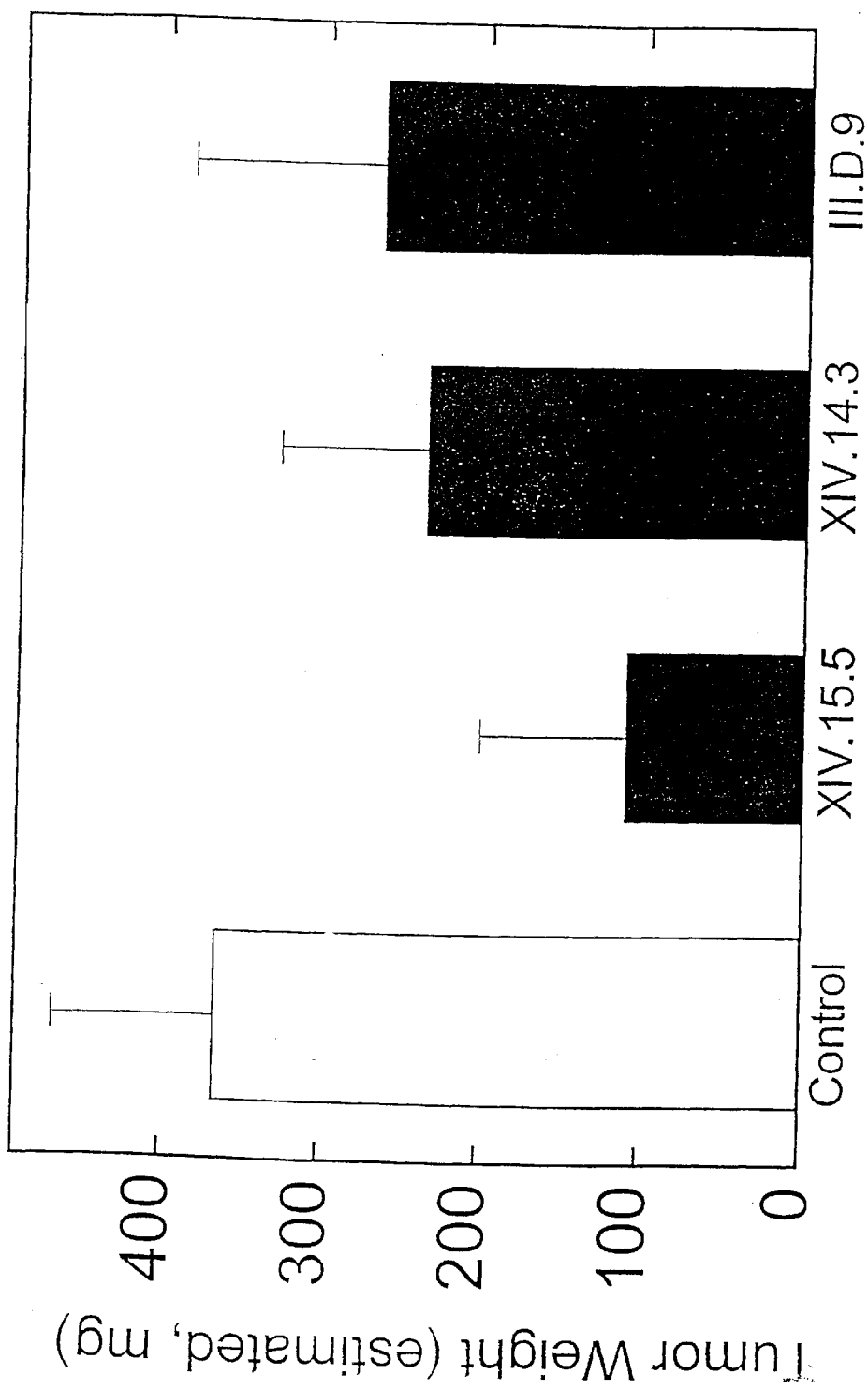

1 Claim, 7 Drawing Sheets ated with Anti-MIF Neutralizing Monoclonal
THERAPEUTIC USES OF FACTORS WHICH INHIBIT OR NEUTRALIZE MIF ACTIVITY The present application is a continuation-in-part of U.S. patent application Ser. No. 08/462,350, filed Jun. 5, 1995, abn., which is a continuation-in-part of U.S. patent application Ser. No. 08/243,342, filed May 16, 1994, abn., which is a continuation-in-part of U.S. patent application Ser. No. 08/063,399, filed May 17, 1993 (now abandoned), each of which is incorporated by reference herein in its entirety.

1. INTRODUCTION

The present invention relates to methods of treating disorders related to cellular overproliferation comprising neutralizing the production or activity of macrophage migration inhibitory factor (MIF). The invention also relates to therapeutic compositions comprising factors which inhibit or neutralize MIF activity, such as, MIF antisense RNA molecules and MIF monoclonal antibodies and derivatives or analogs thereof. The invention further relates to the uses of such compositions and methods for the treatment of malignancies, including, but not limited to, B and T cell lymphomas.

2. BACKGROUND OF THE INVENTION

MIF was the first lymphokine to be discovered and was originally identified by its ability to prevent the migration of guinea pig macrophages in vitro (Bloom & Bennett, 1966, Science 153:80–82; David, 1966, Proc. Natl. Acad. Sci. USA 56:72–77). Given this activity, the role of MIF activity in inflammation and the immune system was investigated, however the precise role of MIF in either local or systemic inflammatory responses has remained largely undefined. Likewise the role of MIF in other physiological and pathophysiological is still enigmatic.

MIF has been reported to be associated with delayed-type hypersensitivity reactions (Bloom & Bennett, 1966, supra; David, 1966, supra), to be produced by lectin-activated T-cells (Weiser et al., 1981, J. Immunol. 126: 1958–1962), and to enhance macrophage adherence, phagocytosis and tumoricidal activity (Nathan et al., 1973, J. Exp. Med. 137: 275–288; Nathan et al., 1971, J. Exp. Med. 133: 1356–1376; Churchill et al., 1975, J. Immunol. 115: 781–785). Unfortunately, many of these studies used mixed culture supernatants that were shown later to contain other cytokines, such as IFN-γ and IL-4, that also have migration inhibitory activity (McInnes & Rennick, 1988, J. Exp. Med. 167: 598–611; Thurman et al., 1985, J. Immunol. 134: 305–309).

Recombinant human MIF was originally cloned from a human T cell library (Weiser et al., 1989, Proc. Natl. Acad. Sci. USA 86: 7522–7526), and has been shown to activate blood-derived macrophages to kill intracellular parasites and tumor cells in vitro, to stimulate IL-1β and TNFα expression, and to induce nitric oxide synthesis (Weiser et al., 1991, J. Immunol. 147: 2006–2011; Pozzi et al., 1992, Cellular Immunol. 145: 372–379; Weiser et al., 1992, Proc. Natl. Acad. Sci. USA 89:8049–8052; Cunha et al., 1993, J. Immunol. 150:1908–1912). Until very recently, however, the lack of a reliable source of purified MIF has continued to hamper investigation of the precise biological profile of this molecule.

3. SUMMARY OF THE INVENTION

The present invention relates to methods of treating disorders related to cellular overproliferation by neutralizing the activity of MIF. In particular, the present invention relates to the treatment of such disorders by suppressing the production or neutralizing the activity of MIF with anti-MIF monoclonal antibodies or suppressing MIF production with MIF antisense RNA molecules. The invention encompasses therapeutic compositions comprising MIF monoclonal antibodies and derivatives and analogs thereof. The invention further encompasses therapeutic compositions comprising MIF antisense RNA molecules and derivatives and analogs thereof.

The invention relates to the uses of therapeutic compositions which inhibit the production or activity of MIF for the treatment or prevention of tumor related disorders. In a specific embodiment of the invention, therapeutic compositions comprising neutralizing MIF monoclonal antibodies are used to treat B and T cell lymphomas.

The invention is based, in part, on the Applicants' unexpected finding that MIF is required for the proliferation of T cells in vitro. Neutralizing monoclonal antibodies (mAbs) against MIF directly inhibited the proliferation of anti-CD3 induced primary T cells. These results suggest that MIF functions as a cellular growth factor and that MIF plays a role in regulating cellular proliferation.

The invention is further based on the Applicants' surprising discovery that the administration of neutralizing monoclonal antibodies to MIF inhibits the growth of tumors in a murine B cell lymphoma model. These observations indicate an unexpected involvement of MIF in regulating cell cycle and cell growth in vivo at the organismal level. These results suggest that neutralizing the activity of MIF has significant antitumor activity. In addition, the invention is based on the Applicant's discovery that anti-MIF factors inhibit cellular factors required for tumor establishment, such as, the establishment of tumor neovascularization.

The invention is illustrated by working examples which, among other things, demonstrate that MIF monoclonal antibodies have significant antitumor activity in vivo in a murine B cell lymphoma model.

4. BRIEF DESCRIPTION OF THE DRAWINGS

FIG. 1. Inhibition of Initial Lymphoma Outgrowth In Vivo by Treatment with Anti-MIF Neutralizing Monoclonal Antibodies. FIG. 1 shows the mean day 7 estimated tumor weight for anti-MIF treated and isotype control groups. B cell lymphoma cells (38C13 cells, provided by J. D. Kemp, Dept. of Pathology, U. of IA) were collected from exponential growth phase culture (RPMI/10% FBS), centrifuged 10 min at 300×g, washed twice with PBS, and adjusted to a density of $1\times10^5$ cells/ml. A 38C13 suspension ($5\times10^4$ cells) was injected i.d. using a 1 ml syringe fitted with a 27-gauge needle. Within 30 min, mice received a 0.2 ml (0.3 mg) i.p. injection of either an $IgG_1$ isotype control antibody (Pharmingen; San Diego, Calif.) or an anti-MIF monoclonal antibody XIV.15.5, XIV.14.3 or III.D.9 (provided by C. Metz, Dept. of Med. Biochemistry, The Picower Institute). Antibody injections were repeated every 48 hours for 6 days. Tumor weight was estimated from measurements taken after 7 days using Vernier calipers according to the following formula: tumor weight (in grams)=(width, cm)$^2$× (length, cm)/2 as per Taetle et al., 1987, Cancer Treatment Reports 71:297–304. Mice were euthanized by $CO_2$ asphyxiation and tumors were excised and weighed.

Figure 2:
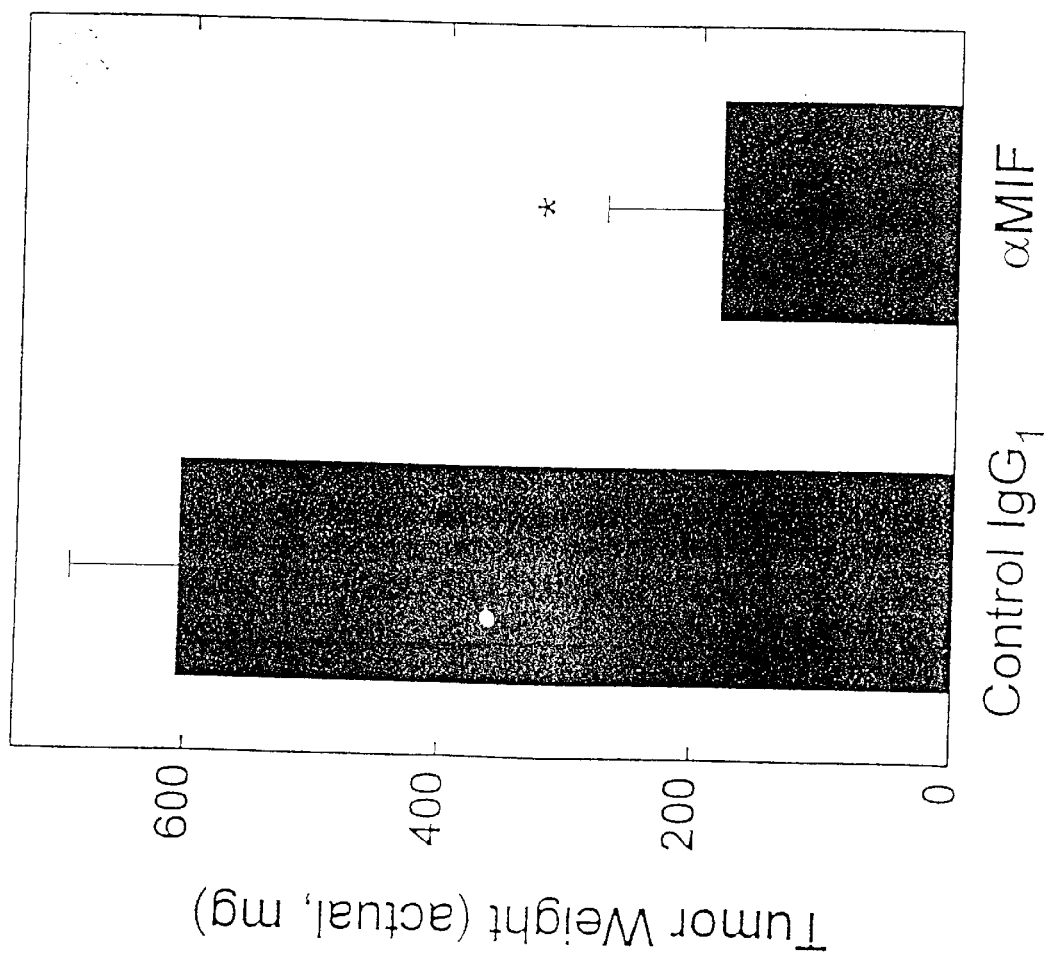

FIG. 2. Inhibition of Initial lymphoma Outgrowth In Vivo by Treatment with Anti-MIF Neutralizing Monoclonal Antibodies. FIG. 2 shows mean wet weight of tumor masses dissected from anti-MIF (XIV.15.5) and control treated groups. The tumors were harvested from the animals described in FIG. 1.

Figure 3:
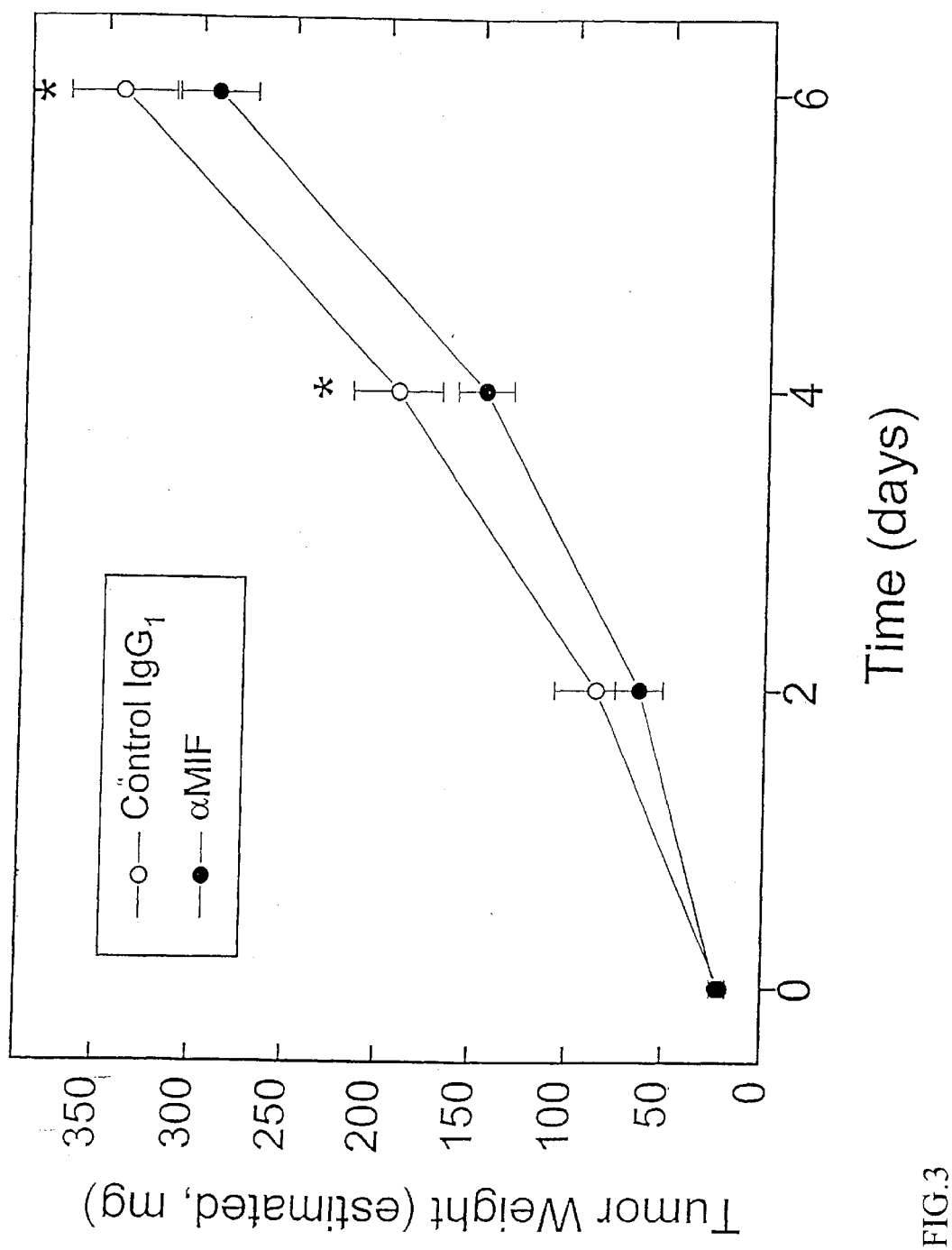

FIG. 3. Inhibition of Established Lymphoma Growth In Vivo by Treatment with Anti-MIF Neutralizing Monoclonal Antibodies. In these experiments, the experimental protocol described in FIG. 1 was followed except that the tumors were allowed to grow for 96 hours to a mean size of approximately 0.01 cm$^3$ before treatment was begun. The tumor-bearing mice were then distributed into groups whose tumors displayed a similar mean tumor size. Treatment of the mice and measurement of the tumors was conducted in a manner as in the initial lymphoma outgrowth experiments described in FIG. 1. Data on the tumor size are plotted every 48 hours from day 0 (time of first antibody (XIV.15.5) injection, 4 days after 38C13 cell injection) to day 6.

Figure 4:
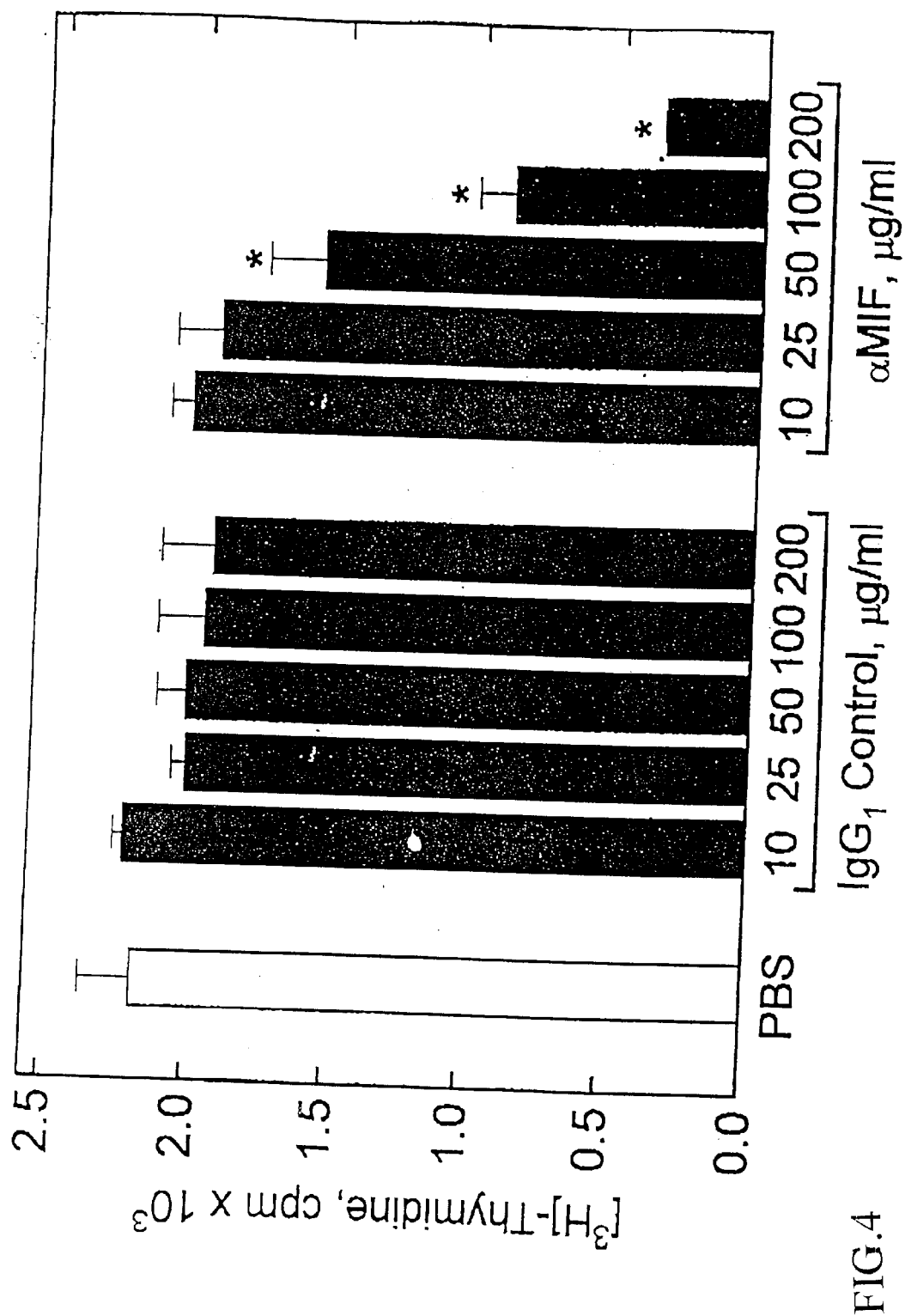

FIG. 4. Inhibition of proliferation of human endothelial cells in vitro with anti-MIF neutralizing monoclonal antibodies. Proliferating human microvascular endothelial cells (fourth passage) (Clonetics; San Diego, Calif.) (5,000/well in a 96-well plate) were incubated with 10–200 μg/ml of IgG$_1$ Control (Sigma; St. Louis, Mo.) or anti-MIF neutralizing monoclonal antibody XIV.15.5 in Endothelial Cell Growth Medium containing 1% fetal bovine serum (ECG-1) for three hours. The proliferative activity of these cultures was measured by the incorporation of [$^3$H]thymidine (4 μCi/ml) into DNA as measured by liquid scintillation counting.

Figure 5:
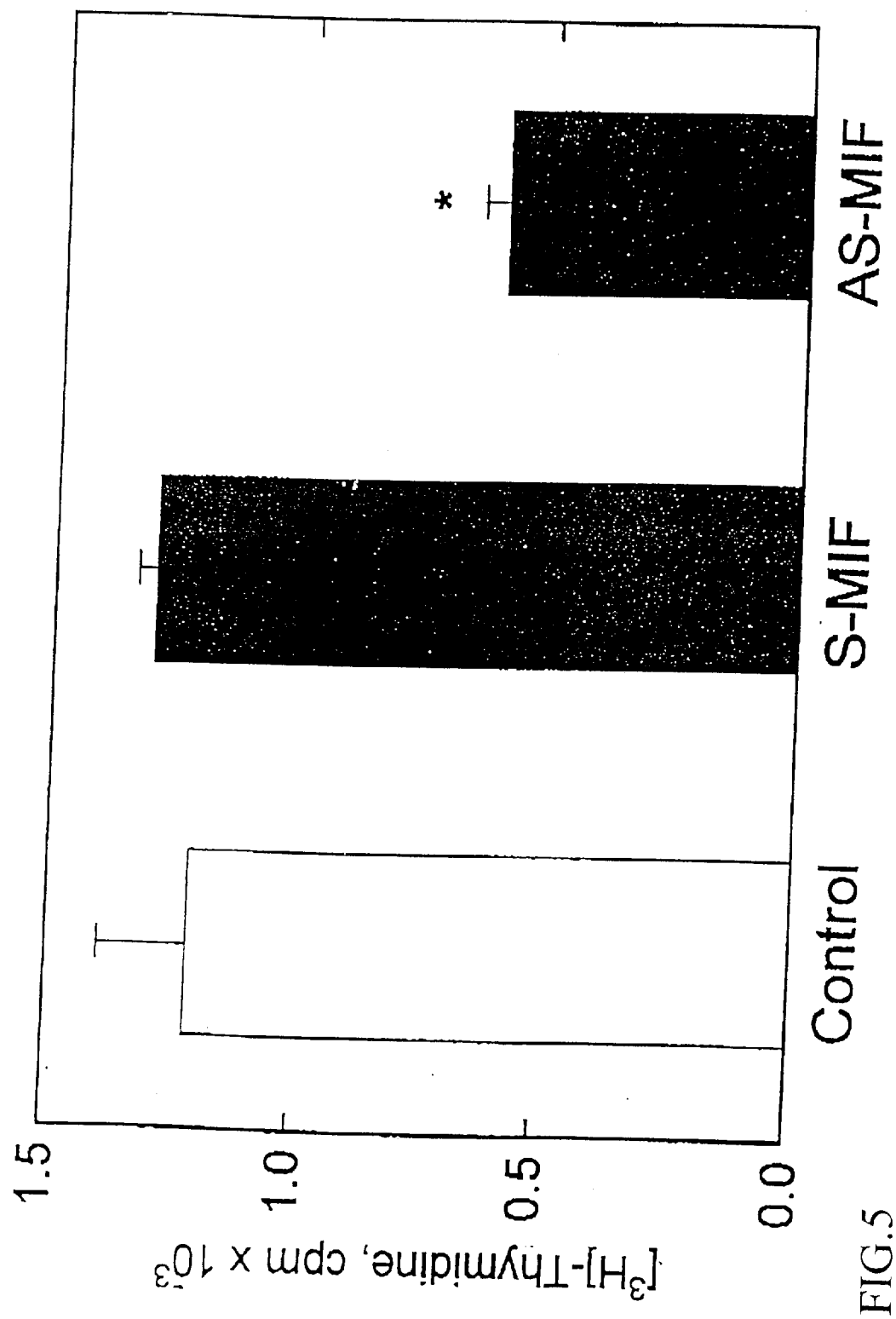

FIG. 5. Inhibition of Proliferation of Human Endothelial Cells In Vitro With MIF Antisense Oligonucleotides. Proliferating human microvascular endothelial cells (fourth passage; Clonetics), cultured in ECG-1 (5,000/well in a 96-well plate), were transfected with the following phosphorothionate oligonucleotides [SEQ ID NOS. 1 and 2] (10 μg/ml; Oligo's etc.; Wilsonville, Oreg.) using Lipofectin reagent per the manufacture's protocol (Gibco; Gaithersburg, Md.):

S-MIF: 5'-GCC-ATC-ATG-CCG-ATG-TTC-AT-3' [SEQ ID NO. 1] (SENSE, HUMAN MIF)
AS-MIF: 5'-ATG-AAC-ATC-GGC-ATG-ATG-GC-3' [SEQ ID NO. 2] (ANTI-SENSE, HUMAN MIF)

After 16 hours, the proliferative activity of these cultures was measured over the subsequent eight hours by the incorporation of [$^3$H]thymidine (4 μCi/ml) into DNA as measured by liquid scintillation counting.

Figure 6:
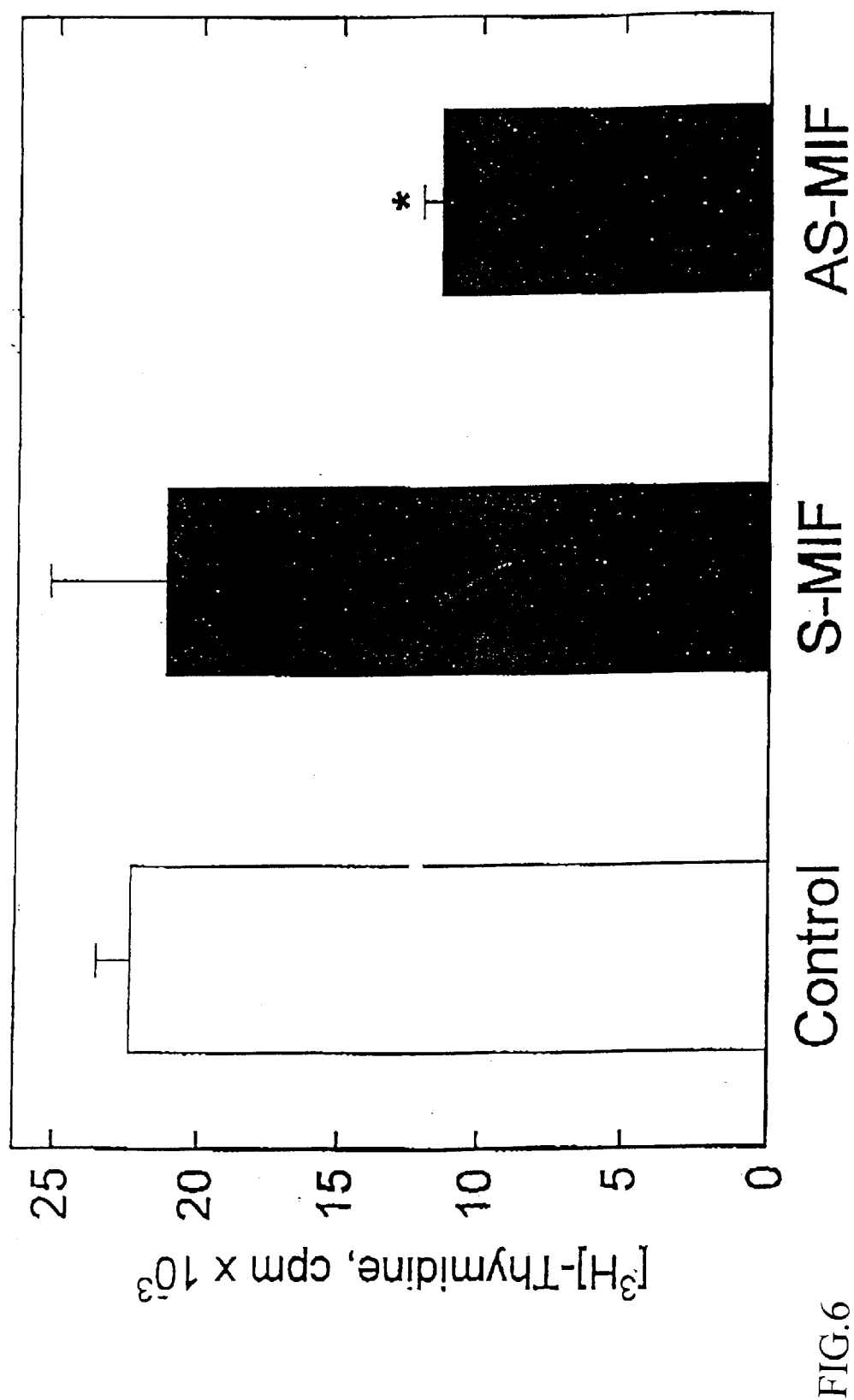

FIG. 6. Inhibition of Proliferation of Myelogenous Leukemia Cells With MIF Antisense Oligonucleotides. Log phase proliferating K-562 chromic myelogenous leukemia cell cultures (5,000 cells/well in a 96-well plate; obtained from ATCC; Rockville, Md.) were transfected with the following phosphorothionate oligonucleotides [SEQ ID NOS. 1 and 2] (10 μg/ml; Oligo's etc.) using Lipofectin reagent per the manufacture's protocol (Gibco):

S-MIF: 5'-GCC-ATC-ATG-CCG-ATG-TTC-AT-3' [SEQ ID NO. 1] (SENSE, HUMAN MIF)
AS-MIF: 5' ATG-AAC-ATC-GGC-ATG-ATG-GC-3' [SEQ ID NO. 2] (ANTI-SENSE, HUMAN MIF)

After 16 hours incubation under standard cell culture conditions (37° C., 5% CO$_2$ in humidified air atmosphere) the proliferative activity of these cultures was measured over the subsequent eight hours by the incorporation of [$^3$H] thymidine (4 μCi/ml; DuPont) into DNA as measured by liquid scintillation counting.

Figure 7:
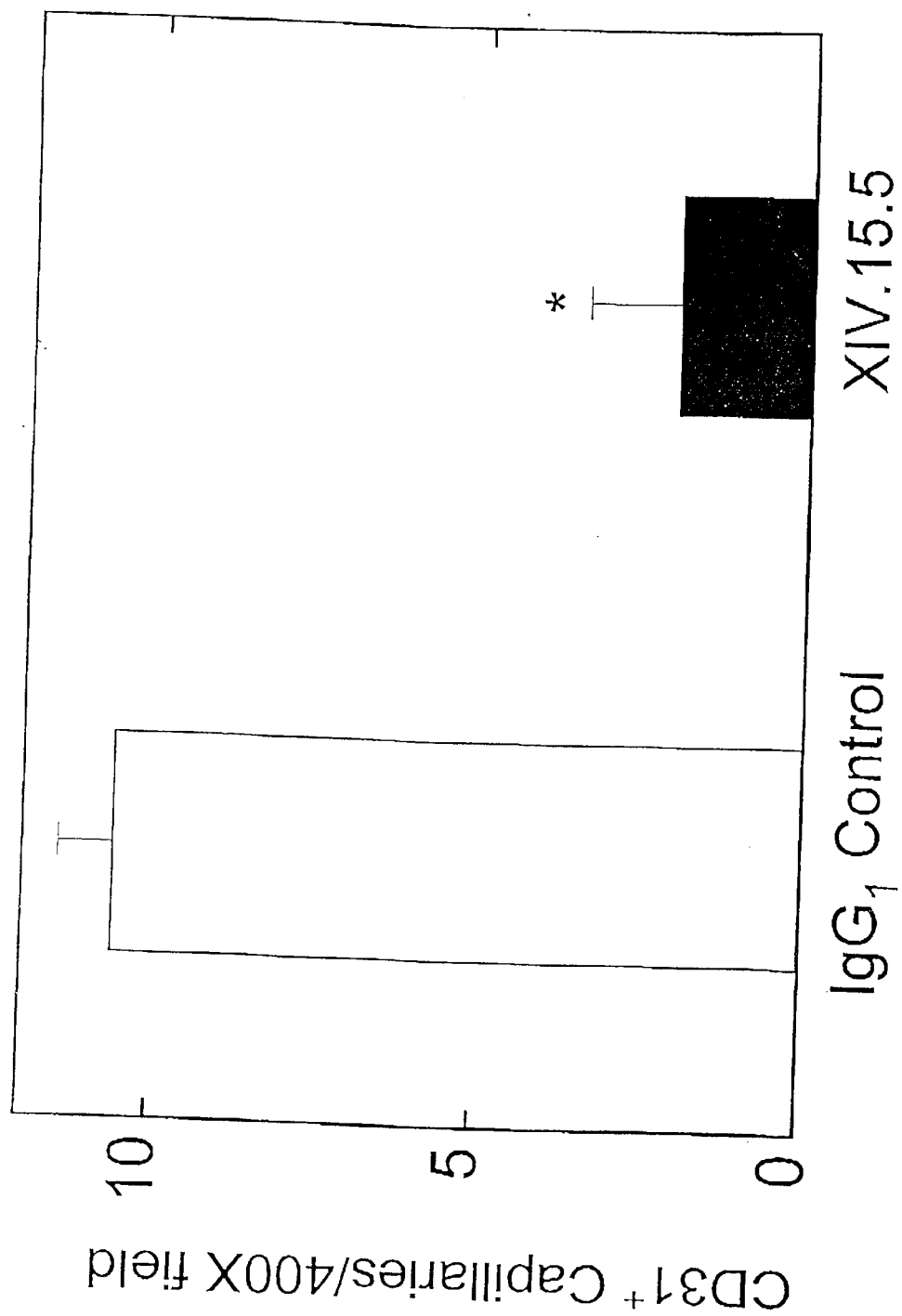

FIG. 7. Inhibition of Tumor Vascularization By Treatment With Anti-MIF Antibodies In Vivo. A comparison of the mean number of CD31-positive capillary profiles per high-power field (400×) in immunohistochemically stained sections of tumors harvested from anti-MIF mAb-treated versus control Ab-treated animals was made. The results clearly demonstrate that the tumors growing in anti-MIF antibody-treated animals, in addition to being smaller than those occuring in control antibody-treated animals, are significantly less vascularized on a per unit volume basis.

5. DETAILED DESCRIPTION OF THE INVENTION

The present invention relates to methods of treating disorders related to cellular overproliferation by neutralizing the production or activity of MIF. The invention also relates to therapeutic compositions comprising factors which inhibit MIF release or which inhibit or neutralize MIF activity, such as, MIF antisense RNA molecules and MIF monoclonal antibodies and derivatives or analogs thereof.

The invention relates to the uses of therapeutic compositions which inhibit the activity of MIF for the treatment or prevention of tumor related disorders. In a specific embodiment of the invention, therapeutic compositions comprising neutralizing MIF monoclonal antibodies or MIF antisense RNA molecules are used to treat B and T cell lymphomas.

The present invention also relates to therapeutic and diagnostic methods and compositions based on anti-MIF monoclonal antibodies and MIF antisense RNA molecules. The invention encompasses therapeutic compositions comprising MIF antisense RNA molecules and MIF monoclonal antibodies and derivatives and analogs thereof.

The invention provides for treatment or prevention of disorders related to cellular overproliferation (e.g., cancer and hyperproliferative disorders) by administering factors which inhibit the release of or neutralize the activity of MIF. The methods of the present invention also relate to the treatment of premalignant conditions, benign tumors, hyperproliferative disorders and benign dysproliferative disorders. Disorders and diseases to be treated by the compositions of the present invention also include but not limited to, B and T cell lymphomas, skin cancer, brain tumors, bone cancer, esophageal cancer, stomach cancer, renal carcinoma, bladder cancer, breast cancer, colon cancer, lung cancer, melanoma, nasopharyngeal cancer, osteocarcinoma, ovarian cancer and uterine cancer.

The present invention also encompasses pharmaceutical compositions comprising a therapeutically effective amount of an antibody that immunospecifically binds to MIF. The invention further encompasses pharmaceutical compositions comprising a therapeutically effective amount of a fragment or derivative of an antibody that contains a binding domain that immunospecifically binds to MIF.

The neutralization or inhibition of MIF in accordance with the invention may be accomplished in a number of ways, which may include, but are not limited to, the use of factors which bind to MIF and neutralize its biological activity; the use of MIF-receptor antagonists; the use of factors that inhibit the enzymatic activity of MIF; the use of compounds that inhibit the release of MIF from cellular sources in the body; and the use of nucleotide sequences derived from MIF coding, non-coding, and/or regulatory sequences to prevent or reduce MIF expression. Any of the foregoing may be utilized individually or in combination to inhibit MIF activity in the treatment of conditions related to cellular overproliferation, and further may be combined with any other antitumor therapy, such as pharmacological, surgical, cytokine, steroids or gene therapy, or any combination thereof.

5.1. The Role of MIF in Controlling Cellular Proliferation

The invention is based, in part, on the Applicants' hypothesis that MIF plays a role in regulating cellular proliferation, and that by specifically neutralizing the activity of MIF, inhibition of cellular proliferation would result. This model is supported by the working examples described in Sections 6, 7 and 8 infra, The invention is based, in part, on the Applicants' unexpected finding that MIF is required for the proliferation of T cells in vitro. Neutralizing monoclonal antibodies (mAbs) against MIF directly inhibited the proliferation of anti-CD3 activated primary T cells, as measured by [$^3$H] thymidine incorporation. These results suggest that MIF functions to regulate the immune system; i.e. activation of T cells. These results may also suggest a role for MIF in regulating cellular proliferation. M. Bacher et al., 1996, Proc. Natl. Acad. Sci. USA 93:7849–7854.

The invention is further based on the Applicants' surprising discovery that the administration of neutralizing monoclonal antibodies against MIF inhibits the growth of tumors in a murine B cell lymphoma model. In addition, the invention is also based on the Applicants' discovery that anti-MIF agents inhibit host-dependent processes required for tumor establishment, such as, the establishment of tumor neovascularization. These observations indicate an unexpected involvement of MIF in regulating cell growth, cell cycle and tumorigenesis. These results suggest that neutralizing the production, release or activity of MIF has significant antitumor activity.

5.2. Inhibitors of MIF Activity

The neutralization or inhibition of MIF in accordance with the invention may be accomplished in a number of ways, which may include, but are not limited to, the use of factors which bind to MIF and neutralize its biological activity; the use of MIF-receptor antagonists; MIF enzymatic inhibitors; the use of compounds that inhibit MIF enzymatic activity; the use of compounds that inhibit the release of MIF from cellular sources in the body; and the use of nucleotide sequences derived from MIF coding, non-coding, and/or regulatory sequences to prevent or reduce MIF expression. See co-pending application Ser. No. 08/462,350, filed Jun. 5, 1995, which is incorporated herein in its entirety by reference.

5.2.1. MIF Monoclonal Antibodies

The MIF neutralizing factors of the present invention may include, but are not limited to anti-MIF antibodies, antibody fragments, MIF receptors, and MIF receptor fragments.

Various procedures known in the art may be used for the production of antibodies to epitopes of recombinantly produced (e.g., using recombinant DNA techniques described infra), or naturally purified MIF. Neutralizing antibodies, e.g., those which inhibit biological activities of MIF by competing for or sterically obstructing the MIF epitopes involved in binding of cellular receptors are especially preferred for diagnostics and therapeutics. Such antibodies include but are not limited to polyclonal, monoclonal, chimeric, single chain, and fragments produced by an Fab expression library.

For the production of antibodies, various host animals may be immunized by injection of MIF and/or a portion of MIF. Such host animals may include but are not limited to rabbits, mice, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

Monoclonal antibodies to MIF may be prepared by using any technique which provides for the production of antibody molecules by continuous cell lines in culture. These include but are not limited to the hybridoma technique originally described by Kohler and Milstein, (Nature, 1975, 256:495–497), the human B-cell hybridoma technique (Kosbor et al., 1983, Immunology Today, 4:72; Cote et al., 1983, Proc. Natl. Acad. Sci., 80:2026–2030) and the EBV-hybridoma technique (Cole et al., 1985, Monoclonal Antibodies and Cancer Therapy, Alan R. Liss, Inc., pp. 77–96). In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. Alternatively, techniques described for the production of single chain antibodies (U.S. Pat. No. 4,946,778) can be adapted to produce MIF-specific single chain antibodies.

The hybridoma technique has been utilized to generate anti-MIF monoclonal antibodies. Hybridomas secreting IgG monoclonal antibodies directed against both human and murine forms of MIF have been isolated and characterized for their ability to neutralize MIF biological activity. Anti-MIF monoclonal antibodies were shown to inhibit the stimulation of macrophage-killing of intracellular parasites. The anti-MIF monoclonal antibodies have also been utilized to develop a specific and sensitive ELISA screening assay for MIF. Both the anti-MIF monoclonal antibodies and the ELISA assay may be used in the diagnosis and/or treatment of inflammatory responses and shock.

Antibody fragments which recognize specific MIF epitopes may be generated by known techniques. For example, such fragments include but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., 1989, Science, 246:1275–1281) to allow rapid and easy identification of monoclonal Fab fragments with the desired specificity for MIF.

5.2.2. Inhibitors of MIF Activity

The present invention relates to the use of factors which neutralize or inhibit MIF activity in a number of ways, which may include, but are not limited to, the use of factors which bind to MIF and neutralize its biological activity; the use of MIF-receptor antagonists; the use of compounds that inhibit MIF enzymatic activity; the use of compounds that inhibit the release of MIF from cellular sources in the body; and the use of nucleotide sequences derived from MIF coding, non-coding, and/or regulatory sequences to prevent or reduce MIF expression. Such factors may include, but are not limited to anti-MIF antibodies, antibody fragments, MIF binding proteins and receptors, and MIF receptor fragments.

Various procedures known in the art may be used for the production of antibodies to epitopes of recombinantly produced (e.g., using recombinant DNA techniques described infra), or naturally purified MIF. Neutralizing antibodies, e.g., those which inhibit biological activities of MIF by competing for or sterically obstructing the binding sites of the MIF receptor are especially preferred for diagnostics and therapeutics. Such antibodies include but are not limited to polyclonal, monoclonal, chimeric, single chain, Fab fragments and fragments produced by an Fab expression library.

For the production of antibodies, various host animals may be immunized by injection with MIF and/or a portion of MIF. Such host animals may include but are not limited to rabbits, mice, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

Monoclonal antibodies to MIF may be prepared by using any technique which provides for the production of antibody molecules by continuous cell lines in culture. These include but are not limited to the hybridoma technique originally described by Kohler and Milstein, (Nature, 1975, 256:495–497), the human B-cell hybridoma technique (Kosbor et al., 1983, Immunology Today, 4:72; Cote et al., 1983, Proc. Natl. Acad. Sci., 80:2026–2030) and the EBV-hybridoma technique (Cole et al., 1985, Monoclonal Antibodies and Cancer Therapy, Alan R. Liss, Inc., pp. 77–96). In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. Alternatively, techniques described for the production of single chain antibodies (U.S. Pat. No. 4,946, 778) can be adapted to produce MIF-specific single chain antibodies.

The hybridoma technique has been utilized to generate anti-MIF monoclonal antibodies. Hybridomas secreting IgG monoclonal antibodies directed against both human and murine forms of MIF have been isolated and characterized for their ability to neutralize MIF biological activity. Anti-MIF monoclonal antibodies were shown to inhibit the stimulation of macrophage-killing of intracellular parasites. The anti-MIF monoclonal antibodies have also been utilized to develop a specific and sensitive ELISA screening assay for MIF. Both the anti-MIF monoclonal antibodies and the ELISA assay may be used in the diagnosis and/or treatment of inflammatory responses and shock.

Antibody fragments which recognize specific MIF epitopes may be generated by known techniques. For example, such fragments include but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., 1989, Science, 246:1275–1281) to allow rapid and easy identification of monoclonal Fab fragments with the desired specificity to MIF.

5.2.3. MIF-receptor Antagonists

Molecules which inhibit MIF biological activity by binding to MIF receptors may also be utilized for the treatment of conditions involving cytokine-meditated toxicity. Such molecules may include, but are not limited to anti-MIF receptor antibodies and MIF analogs.

Anti-MIF receptor antibodies may be raised and used to neutralize MIF receptor function. Antibodies against all or any portion of a MIF receptor protein may be produced, for example, according to the techniques described co-pending application Ser. No. 08/462,350, filed Jun. 5, 1995, incorporated herein by reference in its entirety.

MIF analogs may include molecules that bind the MIF receptor but do not exhibit biological activity or that otherwise compete against MIF to inhibit MIF biological activity. Such analogs that compete with MIF for binding to the MIF receptor, and, therefore, when used in vivo, may act to block the effects of MIF in regulating cell cycle, growth, proliferation of cell populations, tumorigenesis, or tumor progression. A variety of techniques well known to those of skill in the art may be used to design MIF analogs.

Recombinant DNA techniques may be used to produce modified MIF proteins containing, for example, amino acid insertions, deletions and/or substitutions which yield MIF analogs with only limited or without any biological activity. Alternatively, MIF analogs may be synthesized using chemical methods such as those described in the art (see, for example, Sambrook et al., 1989, Molecular Cloning, A Laboratory Manual, Cold Spring Harbor Press, N.Y.).

MIF binding proteins or MIF-specific cellular receptors and/or cell lines that express such MIF binding partners or MIF receptors may be used to identify and/or assay potential MIF antagonists. For example, one method that may be pursued in the identification of such MIF antagonist molecules would comprise attaching MIF binding protein or receptor molecules to a solid matrix, such as agarose or plastic beads, microtiter wells, or petri dishes, using techniques well known to those of skill in the art, and subsequently incubating the attached MIF receptor molecules in the presence of a potential MIF analog or analogs. After incubating, unbound compounds are washed away, and the MIF receptor-bound compounds are recovered. In this procedure, large numbers of types of molecules may be simultaneously screened for MIF receptor-binding activity. Bound molecules may be eluted from the MIF receptor molecules by, for example, competing them away from the MIF receptor molecules with the addition of excess MIF, changing the pH or osmotic strength of the buffer or adding chaotropic agents. The binding/elution steps bring about a partial purification of the molecules of interest.

In order to continue the purification process, the eluted molecules may be further fractionated by one or more chromatographic and/or other separation techniques well known in the art until the molecule(s) of interest is (are) purified to the extent necessary.

Alternatively, screening of peptide libraries with recombinantly produced MIF binding proteins and receptors and/or MIF receptor fragments may be used to identify potential MIF analogs. Once peptides that bind such MIF receptor molecules are identified using this screening technique, their effects on MIF-dependent regulation of cell growth, cell cycle, proliferation of cell populations or tumorigenesis may be assayed using cells lines such as those described in this Section, or alternatively, may be evaluated using normal experimental animal models or transgenic animals such as those described in co-pending application Ser. No. 08/462, 350, incorporated herein by reference in its entirety. Small organic molecules which mimic the activity of such peptides are also within the scope of the present invention.

Random peptide libraries consist of diverse combinations of amino acids, and such libraries may be attached to a suitable small particulate solid phase support and used to identify peptides that are able to bind to a given receptor (Lam, K. S. et al., 1991, Nature 354: 82–84). The screening of peptide libraries may have therapeutic value in the discovery of pharmaceutical agents that act to inhibit the biological activity of MIF receptors through their interactions with the given receptor.

Identification of molecules that are able to bind to the MIF receptor may be accomplished by screening a peptide library with recombinant soluble MIF receptor protein. Methods for expression and purification of molecules such as MIF receptors are well known to those of skill in the art. For screening, it is preferred to label or "tag" the MIF receptor molecule. The protein may be conjugated to enzymes such as alkaline phosphatase or horseradish peroxidase or to other reagents such as fluorescent labels which may include fluorescein isothyiocynate (FITC), phycoerythrin (PE) or rhodamine. Conjugation of any given label to the MIF receptor may be performed using techniques that are routine in the art. Alternatively, MIF receptor expression vectors may be engineered to express a chimeric MIF receptor protein containing an epitope for which a commercially available antibody exists. The epitope-specific antibody may be tagged using methods well known in the art including labeling with enzymes, fluorescent dyes or colored or magnetic beads.

The "tagged" MIF receptor or receptor/conjugate is incubated with the random peptide library for 30 minutes to one hour at 22° C. to allow complex formation between MIF receptor and peptide species within the library. The library is then washed to remove any unbound MIF receptor protein. If MIF receptor has been conjugated to alkaline phosphatase or horseradish peroxidase the whole library is poured into a petri dish containing a substrates for either alkaline phosphatase or peroxidase, for example, 5-bromo-4-chloro-3-indoyl phosphate (BCIP) or 3,3',4,4"-diaminobenzidine (DAB), respectively. After incubating for several minutes, the peptide/solid phase-MIF receptor complex changes color, and can be easily identified and isolated physically under a dissecting microscope with a micromanipulator. If a fluorescent tagged MIF receptor molecule has been used, complexes may be isolated by fluorescence-activated sorting. If a chimeric MIF protein expressing a heterologous epitope has been used, detection of the peptide/MIF receptor complex may be accomplished by using a labeled epitope-specific antibody. Once isolated, the MIF receptor conjugate may be eluted off, the peptide support washed, and the identity of the peptide attached to the solid phase support determined by peptide sequencing.

MIF analogs may also be identified using cell lines that express MIF receptor. Such cell lines may be ones which naturally express the receptor, such as RAW 264.7 cells, or alternatively, cell lines that have been engineered using recombinant techniques to express MIF receptor. These cell lines may also be used to evaluate potential MIF analogs identified using MIF receptor binding techniques such as those described above.

With respect to engineered cell lines, a variety of cells may be utilized as host cells for expression of the recombinant MIF receptor, including, but not limited to animal cell systems infected with recombinant virus expression vectors (e.g., adenovirus, vaccinia virus) including cell lines engineered to contain multiple copies of the MIF receptor DNA either stably amplified (e.g., CHO/dhfr) or unstably amplified in double-minute chromosomes (e.g., murine cell lines). In cases where an adenovirus is used as an expression vector, the MIF receptor coding sequence may be ligated to an adenovirus transcription-translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing MIF receptor in infected hosts (e.g., See Logan & Shenk, 1984, Proc. Natl. Acad. Sci. (USA) 81:3655–3659). Alternatively, the vaccinia 7.5K promoter may be used. (See, e.g., Mackett et al., 1982, Proc. Natl. Acad. Sci. (USA) 79: 7415–7419; Mackett et al., 1984, J. Virol. 49: 857–864; Panicali et al., 1982, Proc. Natl. Acad. Sci. 79: 4927–4931).

Specific initiation signals may also be required for efficient translation of inserted MIF receptor coding sequences. These signals include the ATG initiation codon and adjacent sequences. In cases where the entire MIF receptor gene, including its own initiation codon and adjacent sequences, is inserted into the appropriate expression vector, no additional transcriptional control signals may be needed. However, in cases where only a portion of the MIF receptor coding sequence is inserted, exogenous transcriptional control signals, including the ATG initiation codon, must be provided. Furthermore, the initiation codon must be in phase with the reading frame of the MIF receptor coding sequence to ensure translation of the desired insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, Methods in Enzymol. 153: 516–544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins. Appropriate cells lines or host systems can be chosen to ensure the correct modification and processing of the foreign protein expressed. To this end, eukaryotic host cells which possess the cellular machinery for proper processing of the primary transcript, and for any normal glycosylation, and/or phosphorylation of the gene product may be used. Such mammalian host cells include but are not limited to CHO, VERO, BHK, HeLa, COS, MDCK, 293, WI38, etc.

The cell lines may be utilized to screen and identify MIF analogs. Synthetic compounds, natural products, and other sources of potentially biologically active materials can be screened in a number of ways, by, for example, testing a compound's ability to inhibit binding of MIF to a MIF receptor. Standard receptor binding techniques may be utilized for this purpose.

The ability of anti-MIF receptor antibodies and potential MIF analogs to reduce or inhibit MIF biological activity may be assayed in vivo by utilizing animals expressing MIF receptor, for instance, normal animals. Such animals may also include transgenic animal models such as those described in co-pending application Ser. No. 08/462,350.

5.2.4. Other Inhibitors of MIF Activity

Compounds which inhibit the release of MIF can be identified in cell based assays, such as the one described in co-pending application Ser. No. 08/462,350. In general, any pituitary or macrophage cell line that releases MIF in response to a challenge dose of steroid can be used. The assay can be conducted by adding the test compound to the cells in culture which are then challenged for instance with a dose of steroid known to induce MIF release. Test compounds may be administered simultaneously with, or up to several hours before or after the challenge dose so as to identify agents that are useful in inhibiting the MIF response at different stages, i.e., inhibiting release of pre-formed MIF, versus inhibiting de novo synthesis and release, versus inhibiting both.

The conditioned media is then collected from the cultured cells and assayed for MIF; e.g., by immunoassay, including but not limited to an ELISA, Western blot, radioimmunoassay, etc. A reduced amount of MIF in the conditioned media compared to control cultures indicates that the test compound inhibits the steroid-induced release of MIF. Compounds so identified in this assay may be used in combination therapy with steroids to treat inflammation. "Biologically inert" or innocuous compounds, such as the inactive steroids, or steroids which can be used at doses that do not cause undesired side effects, may be preferred for therapeutic use. However, any inhibitory compounds having a good therapeutic index, e.g., low toxicity and little or no side effects may be used.

5.3. Inhibitors of MIF and/or MIF Receptor Gene Expression

Nucleotide sequences derived from the coding, non-coding, and/or regulatory sequences of the MIF and/or MIF receptor genes may be used to prevent or reduce the expression of these genes, leading to a reduction or inhibition of MIF activity. The nucleotide sequence encoding the human MIF protein has been reported ([SEQ ID NO: 3] (see copending application Ser. No. 08/462,350), abandoned, of which application Ser. No. 08/471,546 is a divisional, now patented as U.S. Pat. No. 6,030,015, in which the human MIF nucleotide sequence is presented in FIG. 2 and SEQ. ID. NO: 14). Further, the MIF receptor amino acid sequence provided in co-pending application Ser. No. 08/462,350, may be used to design oligonucleotides for the regulation of MIF receptor genes. Among the techniques by which such regulation of gene expression may be accomplished are, as described below, antisense, triple helix, and ribozyme approaches. Administration of these nucleotide sequences, therefore, may be used to temporarily block expression and/or transcription of the MIF and/or MIF receptor genes as one method of treatment for conditions involving MIF-dependent regulation of cell growth, cell cycle, differentiation or proliferation of cell populations or tumorgenesis.

These approaches which target gene expression may be used alone, in combination with each other, or alternatively, in conjunction with any of the inhibitory MIF-binding and/or MIF receptor antagonist procedures described above. Further, these gene regulation approaches may be used together with anti-TNFα, anti-initiators and/or other anti-cytokine therapies.

5.4. The Generation of MIF Monoclonal Antibodies

The present invention relates in part to the use of neutralizing antibodies which inhibit the ability of MIF to regulate cellular proliferation. Methods useful for generating and testing such antibodies are described below by way of example. The methods of the present invention are not limited to the following specific method to produce neutralizing MIF antibodies.

Hybridomas secreting monoclonal antibodies (MAbs) directed against human and murine forms of MIF were made and isolated according to methods well known in the art. In brief summary, female BALB/c mice were immunized intraperitoneally (i.p.) with recombinant murine or human MIF (10 μg/mouse) in Ribi Adjuvant (Ribi Immunochem.). During the immunization and boost period, mice were tail-bled and serum anti-MIF antibody titers, as well as isotype distribution (IgM vs IgG), were assayed by microtiter plate-based direct enzyme-linked immunosorbent assay (ELISA) methods on wells with immobilized recombinant MIF (250 ng/ml; 55 μl/well) as antigen. Immunized mice were given booster injections of recombinant MIF (10 μg/mouse) in Ribi Adjuvant at least four times before spleens were removed for fusion. Three days before spleen cell fusion with mouse myeloma cells (P3X63Ag8.653; American Type Culture Collection) using polyethylene glycol (Boerhinger Mannheim), mice were boosted i.p. with both murine and human MIF (10 μg in PBS). Hybridomas were expanded under HAT (hypoxanthine, aminopterin, and thymidine; GIBCO) selection medium (DMEM containing HAT, 10% Condimed (Boerhinger Mannheim), 20% FBS (Hyclone), and antibiotics (penicillin, streptomycin; GIBCO) for two to three weeks. Culture supernatants from growing hybridomas were screened for anti-MIF antibodies by direct ELISA methods with immobilized recombinant MIF.

Immunoreactivity of antibodies from anti-MIF positive clones was further analyzed by Western immunoblotting techniques, and high-titer producing hybridomas were chosen for re-cloning by limiting dilution. Anti-MIF monoclonals were isotyped using Screentype ELISA (Boehringer Mannheim). Hybridomas secreting desired monoclonal antibodies (IgG-type) were grown as ascites in BALB/c mice, and MAb's were purified using T-gel chromatography (Pierce). Several IgM-type anti-MIF monoclonal antibodies were identified but not further characterized. Several IgG-secreting hybridomas were isolated and characterized (Table I).

TABLE I

| | Reactivity with | | |
| --- | --- | --- | --- |
| | Human MIF | Murine MIF | IgG Subtype |
| VIIG3 | − | + | IgG2b |
| IXD11 | − | + | IgG2a |
| XB2 | − | + | IgG3 |
| XID5 | − | + | IgG2b |
| XIG2 | − | + | IgG3 |
| VD8 | − | + | IgG2b |
| IID9 | + | + | IgG1 |
| IIID9 | + | + | IgG1 |
| XIF7 | + | + | IgG2b |
| I31 | + | + | IgG1 |
| IV2.2 | + | + | IgG1 |
| XI7 | + | + | n.d. |
| XII15.6 | + | + | IgG1 |
| XIV15.4 | + | + | IgG1 |

5.4.1. Test for Anti-MIF Neutralization Activity

Purified anti-MIF monoclonal antibodies were first tested for neutralization activity in a macrophage killing assay. Thioglycollate-elicited mouse peritoneal macrophages were obtained from BALB/c mice, allowed to adhere for 4 hours, and then infected with the intracellular parasite *Leishmania major* at a parasite:macrophage ratio of 8:1. After washing, infected macrophage cultures were treated with recombinant human MIF (which enhances macrophage-killing of intracellular parasites in a dose-dependent fashion when compared to culture medium controls) with or without added VIIG3 or XID5 monoclonal anti-MIF antibodies (25 μg/ml). Both antibodies were found to neutralize the MIF-enhanced killing of *L. major* by about 50%.

In separate experiments, purified monoclonal anti-MIF antibodies were tested for MIF neutralizing activity in a [$^3$H]-thymidine incorporation assay with primary murine T cells cultured on anti-CD3 IgG-coated (Pharmingen) tissue culture plates. Briefly described, this assay employed BALB/c spleen cells that were isolated using murine T cell enrichment columns (R&D) and grown on anti-CD3 IgG-coated 96 well micro-titer plates in RPMI containing 10% FBS, antibiotics (penicillin, streptomycin) and L-glutamine together with anti-MIF or control mouse monoclonals antibodies. After 48 hours, T cells were pulsed with [$^3$H]-thymidine for 16 to 18 hours, harvested and counted by beta-scintillation counting methods. As a positive control, anti-IL-2 monoclonal antibodies (Genzyme) were added to inhibit proliferation and associated [$^3$H]-thymidine incorporation. Both the VIIG3 and the XID5 antibodies decreased thymidine incorporation by about 20%; anti-IL-2 treatment reduced [$^3$H]-thymidine incorporation by about 75%.

5.4.2. Development of Quantitative Sandwich Elisa for MIF

A MIF-specific "sandwich" ELISA technique was developed, based on the trapping of MIF by immobilized VIIG3 antibody followed by detection with a rabbit polyclonal anti-MIF antiserum. This assay was performed as follows:

Immulon II (Dynatech) ELISA plate wells were coated with 10–15 µg/ml MAb (VIIG3) in PBS (65 µl/well); the MAb had been purified from ascites using T-gel absorbent (Pierce). Plates were sealed and incubated overnight at room temperature. Wells were then blocked with Superblock (Pierce) containing 2% goat serum (140–150 µl/well) for 1–2 hours at room temperature. Plates were washed using an automated ELISA plate washer (twice with TBS containing 0.05% Tween20 using 200 µl/well). MIF samples and standards were prepared in 0.5 ml or 1.5 ml eppendorf tubes by adding Tween20 to culture supernatants to a final concentration of 0.2%. Cell lysates were likewise diluted in TBS buffer with Tween20 at a final concentration of 0.2%. Standards were prepared similarly by diluting purified recombinant murine or human MIF in DMEM/1% FBS/0.2% Tween20. Samples and standards were applied to the plate (60 µl/well) and the plate sealed and incubated overnight at 4° C. with gentle shaking. The plate was then washed five times with TBS/0.05% Tween20, and second antibody (e.g. Rabbit 102 anti-murMIF serum, 1:220 in TBS/0.2% Tween20/2% goat serum) added at 60 µl/well. The plate was sealed and incubated 2 hours at room temperature with gentle shaking. All wells were then washed five times with TBS/0.05% Tween20 and tertiary antibody-enzyme conjugate (commercially available goat anti-rabbit IgG-alkaline phosphatase, diluted 1:4000 in TBS/0.2% Tween20/2% goat serum as recommended by the manufacturer, Boehringer Mannheim) was added at 60 µl/well. The plate was covered, incubated for 35 minutes at room temperature, and then washed 5 times with TBS/0.05% Tween20. The assay was then developed with p-nitrophenyl phosphate (pNPP) solution as recommended by the manufacturer (5 mg Sigma 104 tablet in 5 ml AP buffer: 10 mM diethanolamine/0.5 mM MgCl$_2$, pH 9.5). Reaction product was allowed to develop in the dark at room temperature, and read at 405 nm within 15–30 minutes. This assay gives range of sensitivity of about 100 pg/ml–250 ng/ml. It should be noted that for the practice of this "sandwich" technique, various combinations of two or more MIF-specific antibodies may be used to capture and detect MIF in a sample. The immobilized antibody is not restricted to VIIG3 antibody, and the second antibody is not limited to a rabbit antiserum.

5.5. Therapeutic Uses: Treatment and Prevention of Disorders Involving Over-proliferation of Cells The invention provides for treatment or prevention of various diseases and disorders by administration of an anti-MIF monoclonal antibody. A MIF monoclonal antibody can be used for therapeutic purposes for the treatment of cancer and hyperproliferative or dysproliferative disorders. Malignancies that may be treated by anti-MIF monoclonal antibodies include but are not limited to those listed in Table II.

TABLE II

MALIGNANCIES AND RELATED DISORDERS

Leukemia
  Acute Leukemia
    Acute Lymphocytic Leukemia
    Acute Myelocytic Leukemia
      Myeloblastic
      Promyeloblastic
      Myelomonocytic
      Monocytic
      Erythroleukemia
  Chronic Leukemia
    Chronic Myelocytic Leukemia
    Chronic Lymphocytic Leukemia
Polycythema Vera
Lymphoma
  Hodgkins disease
  Non-Hodgkins disease
Multiple Myeloma
Solid tumors
  Sarcomas and Carcinomas
    Fibrosarcoma
    Mxycosarcoma
    Liposarcoma
    Chondrosarcoma
    Osteogenic Sarcoma
    Osteosarcoma
    Chordoma
    Angiosarcoma
    Endotheliosarcoma
    Ewing's Tumor
    Colon Carcinoma
    Colorectal Carcinoma
    Pancreatic Cancer
    Breast Cancer
    Ovarian Cancer
    Prostate Cancer
    Squamous Cell Carcinoma
    Adenocarcinoma
    Sweat Gland Carcinoma
    Sebaceous Gland Carcinoma
    Papillary Carcinoma
    Wilm's Tumor
    Cervical Cancer
    Lung Carcinoma
    Small Cell Lung Carcinoma
    Epithelial Carcinoma
  Melanoma
  Neuroblastoma
  Angiomas
Diabetic Retinopathy In specific embodiments of the present invention, B and T cell lymphomas are treated or prevented. In other specific embodiments, malignancy or dysproliferative changes or hyperproliferative disorders are treated or prevented in the head, neck, cervix, kidney, stomach, skin, ovary, bladder, breast, colon, lung or uterus. In other specific embodiments, sarcoma, or leukemia is treated or prevented. In another particular embodiments, osteosarcoma or renal cell carcinoma is treated or prevented.

The MIF monoclonal antibodies of the present invention can also be administered to treat premalignant conditions and to prevent progression to a neoplastic or malignant state, including but not limited to those disorders listed in Table II. Such prophylactic or therapeutic use is indicated in conditions known or suspected of preceding progression to neoplasia or cancer, in particular, where non-neoplastic cell growth consisting of hyperplasia, or dysplasia has occurred. Hyperplasia is a form of controlled cell proliferation involving an increase in cell number in a tissue or organ, without significant alteration in structure or function. Dysplasia is frequently a forerunner of cancer, and is found mainly in the epithelia; it is the most disorderly form of non-neoplastic cell growth, involving a loss in individual cell uniformity and in the architectural orientation of cells. Dysplasia characteristically occurs where there exists chronic irritation or inflammation and is often found in the cervix, respiratory passages, oral cavity, and gall bladder.

Alternatively or in addition to the presence of abnormal cell growth characterized as hyperplasia or dysplasia, the presence of one or more characteristics or a transformed phenotype, or of a malignant phenotype, displayed in vivo or displayed in vitro by a cell sample from a patient, can indicate the desirability of prophylactic/therapeutic administration of anti-MIF monoclonal antibodies. The characteristics of a transformed phenotype include morphology changes, looser substratum attachment, loss of contact inhibition, loss of anchorage dependence, protease release, increased sugar transport, decreased serum requirement, expression of fetal antigens, disappearance of the 250,000 dalton cell surface protein, etc.

In a specific embodiment, leukoplakia, a bernign-appearing hyperplastic or dysplastic lesion of epitbelium, or Bowen's disease, a carcinoma in situ, are pre-neoplastic lesions indicative of the desirability of prophylactic intervention.

5.6. Pharmaceutical Formulations and Routes of Adminiatration

The compounds of the present invention, including but not limited to, anti-MIF antibodies, have utility in pharmacological compositions for the treatment and prevention of cell overproliferation disorders.

A compound of the invention can be administered to a human patient by itself or in pharmaceutical compositions where it is mixed with suitable carriers or excipients at doses to treat or ameliorate various conditions involving cellular overproliferation. A therapeutically effective dose further refers to that amount of the compound sufficient to inhibit tumor growth. Therapeutically effective doses may be administered alone or as adjunctive therapy in combination with other treatments for tumor growth or associated diseases. Techniques for the formulation and administration of the compounds of the instant application may be found in "Remington's Pharmaceutical Sciences" Mack Publishing Co., Easton, Pa., latest addition.

5.6.1. Routes of Administration

Suitable routes of administration may, for example, include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections, and optionally in a depot or sustained release formulation.

Furthermore, one may administer the agent of the present invention in a targeted drug delivery system, for example in a liposome coated with an anti-CD4 antibody to target T cell lymphomas. The liposomes will be targeted to and taken up selectively by cells expressing CD4.

5.6.2. Composition/Formulation

The pharmaceutical compositions of the present invention may be manufactured in a manner that is itself known, e.g., by means of conventional mixing, dissolving, dragee-making, levitating, emulsifying, encapsulating, entrapping, or lyophilizing processes.

Pharmaceutical compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers, such as Hank's solution, Ringer's solution, or physiological saline buffer. For transmucosal administration, penetrants appropriate to the barrier to be permeated are used in the formulation. Such penetrants are known in the art.

For oral administration, the compounds can be formulated readily by combining the active compounds with pharmaceutically acceptable carriers well known to those in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid- or gel-phase carriers or excipients. Examples of such carriers or excipients include but are not limited to calcium carbonate, calcium phosphate, various sugars, starches, cellulose derivatives, gelatin, and polymers such as polyethylene glycols.

Many of the compounds of the invention identified as neutralizers of MIF activity may be provided as salts with pharmaceutically compatible counterions. Pharmaceutically compatible salts may be formed with many acids, including but not limited to hydrochloric, sulfuric, acetic, lactic, tartaric, malic, succinic, etc.; or bases. Salts tend to be more soluble in aqueous or other protonic solvents that are the corresponding free base forms. Examples of pharmaceutically acceptable salts, carriers or excipients are well known to those skilled in the art and can be found, for example, in Remington's Pharmaceutical Sciences, 18th Edition, A. R. Gennaro, Ed., Mack Publishing Co., Easton, Pa., 1990. Such salts include, but are not limited to, sodium, potassium, lithium, calcium, magnesium, iron, zinc, hydrochloride, hydrobromide, hydroiodide, acetate, citrate, tartrate and malate salts, and the like.

5.6.3. Effective Dosage

Pharmaceutical compositions suitable for use in the present invention include compositions wherein the active ingredients are contained in an effective amount to achieve their intended purpose. More specifically, a therapeutically effective amount means an amount effective to prevent or inhibit development or progression of cancer or hyperproliferative disease in the subject being treated. Determination of the effective amounts is well within the capability of those skilled in the art, especially in light of the detailed disclosure provided herein.

For any compound used in the method of the invention, the therapeutically effective dose can be estimated initially from cell culture assays. Such information can be used to more accurately determine useful doses in humans.

A therapeutically effective dose refers to that amount of the compound that results in a reduction in the development of cancer, a tumor, or a hyperproliferative disease, or of symptoms thereof or that prolonged survival in a patient. Toxicity and therapeutic efficacy of such compounds can be determined by standard pharmaceutical, pharmacological, and toxicological procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds which exhibit high therapeutic indices are preferred. The data obtained from cell culture assays or animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (See e.g. Fingl et al., 1975, in "The Pharmacological Basis of Therapeutics", Ch. 1 p. 1).

Dosage amount and interval may be adjusted individually to provide plasma levels of the active moiety which are sufficient to maintain the desired modulating effects, or minimal effective concentration (MEC). The MEC will vary for each compound but can be estimated from in vitro data; e.g., the concentration necessary to achieve a 50–90% inhibition of cell or tumor growth using the assays described herein. Dosages necessary to achieve the MEC will depend on individual characteristics and route of administration. However, HPLC assays, bioassays or immunoassays can be used to determine plasma concentrations.

Dosage intervals can also be determined using the MEC value. Compounds should be administered using a regimen which maintains plasma levels above the MEC for 10–90% of the time, preferably between 30–90% and most preferably between 50–90%.

In cases of local administration for instance, direct introduction into a tumor, or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

5.6.4. Packing

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labelled for treatment of an indicated condition.

6. EXAMPLE

Initial Tumor Outgrowth Experiments in Vivo

For these experiments, treatment of C3H-HeN mice with various anti-MIF mAbs was begun on the same day as tumor implantation. This procedure specifically examines the potential of anti-MIF mAbs to inhibit initial tumor growth and thus is sometimes considered to be a model for metastasis. Various anti-MIF mAbs can be examined for anti-tumor efficacy in this model, as antiproliferative data obtained from in vitro studies might not accurately predict the efficacy of various anti-MIF mAbs in vivo.

The 38C13 B cell lymphoma model is a well established solid tumor model which has been used to assess novel therapeutics against cancer since its initial description in 1977, e.g., J. D. Kemp et al., 1995, Cancer Research 55:3817–3824. The model was accomplished by injecting murine B lymphoma cells intra-dermally (i.d.) into the strain of mice from which they were initially derived (C3H-HeN). Within 10 days, these mice developed a solid lymphoma which is easily measurable.

Using $^3$H-thymidine incorporation assays, Applicants tested the effects of anti-MIF treatment on 38C13 cells in vitro. Neither anti-MIF antibody treatment (with mAb's III.D.9 or XIV.15.5) nor anti-MIF antisense oligonucleotide treatment (using the antisense oligonucleotides described infra) significantly suppressed 38C13 cell proliferation in vitro, suggesting that such anti-MIF therapeutic methods. and agents are not directly anti-proliferative for this tumor cell type. Recognizing, however, that many host-dependent processes contribute to tumorigenesis in vivo however, Applicants further tested the efficacy against tumor growth of agents and methods directed against MIF and applied in vivo.

C3H-HeN mice were anesthetized and then closely clipped on the upper flank. 50,000 log phase 38C13 cells (in 0.05 ml PBS) we injected i.d. with a 1 ml syringe and a 27 g needle. Within 30 minutes, animals received treatment by IP injection of 500 μg of anti-MIF mAbs or of control isotype mAbs, mAb injections were repeated every 48 hours for 4 days. Animals we monitored daily for tumor growth using Vernier calipers. Animals were euthanized using $CO_2$ asphyxiation, tumors are isolated, weighed, and analyzed by histology.

Due to the variability of tumor growth within groups (dependent on precise site of injection, volume of injection) and to provide for obtain statistically evaluation to results, each experimental group comprised five animals and the experiment was conducted three times. In addition to the experimental groups: (i.e., anti-MIF-Ab treated) control groups were studied, for instance a group treated with an antibody isotype control antibody directed against an irrelevant antigen, and a group treated with vehicle alone. Results are shown in FIGS. 1 and 2 demonstrating that interference with the biological activity of MIF, in this case by treating with a monoclonal antibody inhibited solid tumor development, in this case a B cell lymphome in otherwise normal animals.

7. EXAMPLE

Established Tumor Growth Assays in Vivo

To establish whether therapy against MIF is effective against established tumors, Applicants treated tumor cell-innoculated mice after allowing a period of time for tumors to become established.

In these experiments, the same number of tumor cells was injected in the same manner as described above, but tumors were allowed to develop and grow for 6 days to a mean diameter of about 6 mm. After 6 days, treatment of the animals and measurements of tumors then followed the same scheme as above. This procedure will emphasize the activity of anti-MIF mAbs on established tumors.

C3H-HeN mice were anesthetized and then closely clipped on the upper flank. 50,000 log phase 38C13 cells (in 0.05 ml PBS) were injected i.d. with a 1 ml syringe and a 27 g needle. Animals were monitored daily for tumor growth was estimated from measurements taken with Vernier calipers. On the 6th day of the experiment, groups of animals received treatment by IP injection of 500 μg of isotype mAbs, anti-MIF mAbs, or PBS only. Injections were repeated every 48 hours for 4 days. Animals were monitored daily and tumor growth was estimated from measurements taken with Vernier calipers. Animals are euthanized using $CO_2$ asphyxiation, tumors are isolated, weighed, and analyzed by histology.

Due to variability in initial tumor size (dependent on precise site of injection, volume of injection and other factors) and to provide data for statistical evaluation, each experimental and control group numbered 5 animals. As shown in FIG. 3 established tumors grew more slowly in anti-MIF treated animals than in animals treated with control antibody.

The above procedure for assessing the anti-tumor effects of therapy targeted against MIF was repeated under a different dosing schedule, whereby subject tumor-bearing animals were treated with 0.5 mg anti-MIF antibodies or control antibodies twice daily rather than every other day, beginning on Day 6 after tumor cell engraftment. Mean estimated tumor weight did not differ between the groups on Day 6, as measured just before the first antibody injection (45.6±4.6 mg for the isotype control group versus 46.1±3.4 mg for the group scheduled to receive anti-MIF mAb XIV.15.5; mean±sd). By Day 7, however, tumors in the control-treated group had grown significantly mc)re than tumors in the anti-MIF antibody-treated group (246.7±41,4 versus 97.2±12.2, respectively). These data reinforce the conclusion that methods and agents directed tot eh inhibition of MIF, and more particularly treatment with anti-MIF antibodies, are effective to inhibit the growth of established tumors in vivo.

8. EXAMPLE

Inhibition of Tumor Vascularization

These experiments were carried out to determine if anti-tumor therapy directed against MIF, and more particularly, anti-MIF antibodies, exerts an anti-tumor effect through an influence on host-dependent processes that contribute to tumorigenesis rather than or in addition to any direct anti-proliferative effect on tumor cells. Such host dependent processes includes, for instance, angiogenesis to support neovascularization of the growing tumor.

Proliferating human microvascular endothelial cells (fourth passage) (Clonetics; San Diego, Calif.) 5,000/well in a 96-well plate were incubated with 10–200 µg/ml of $IgG_1$ Control (Sigma; St. Louis, Mo.) or anti-MIF neutralizing monoclonal antibody XIV.15.5 (courtesy of Dr. C. Metz, Department of Medical Biochemistry, The Picower Institute for Medical Research; Manhasset, N.Y.) in Endothelial Cell Growth Medium containing 1% fetal bovine serum (ECG-1; Clonetics) for three hours. The proliferative activity of these cultures was measured over the subsequent 16 hours by the incorporation of [$^3$H]thymidine (4 µCi/ml) (DuPont; Boston, Mass.) into DNA as measured by liquid scintillation counting (FIG. 3). Proliferating human microvascular endothelial cells (fourth passage; Clonetics), cultured in ECG-1 (5,000/well in a 96-well plate), were transfected with the following phosphorothionate oligonucleotides (10 µg/ml; Oligo's etc.; Wilsonville, Oreg.) using Lipofectin reagent per the manufacture's protocol (Gibco; Gaithersburg, Md.):

S-MIF: 5'-GCC-ATC-ATG-CCG-ATG-TTC-AT-3' [SEQ ID NO. 1] (SENSE, HUMAN MIF)
AS-MIF: 5'-ATG-AAC-ATC-GGC-ATG-ATG-GC-3' [SEQ ID NO. 2] (ANTI-SENSE, HUMAN MIF)

After 16 hours, the proliferative activity of these cultures was measured over the subsequent eight hours by the incorporation of [$^3$H]thymidine (4 µCi/ml; DuPont) into DNA as measured by liquid scintillation counting (FIG. 5).

Anti-MIF antibodies were shown to be anti-proliferative for human microvascular endothelial cells (FIG. 4), indicating anti-MIF antibodies exert anti-angiogenic activity in vivo.

Relative to sense MIF constructs, anti-sense MIF mRNA inhibited human endothelial cell proliferation in vitro by approximately 50% (FIG. 5). Thus anti-sense MIF mRNA was shown to be anti-proliferative for human endothelial cells indicating anti-sense MIF mRNA exerts anti-angiogenic activity.

These results demonstrate that anti-MIF therapy against cancer may benefit from (1) direct anti-proliferative effects of anti-MIF therapy on tumor cells; and/or (2) inhibition of host-dependent processes, such as angiogenesis, required for tumor initiation, development or progression.

9. EXAMPLE

Inhibition of Proliferation of Leukemia Cells in Vitro

These studies were carried to examine whether anti-MIF therapeutic methods and agents may have direct anti-proliferative effects on tumor cells. In this example K562 cells (chronic human myelogenous leukemia cells) were exposed to anti-sense MIF constructs.

Log phase proliferating K562 chronic myelogenous leukemia cell cultures (5,000 cells/well in a 96-well plate; obtained from ATCC; Rockville, Md.) were transfected with the following phosphorothionate oligonucleotides (10 µg/ml; Oligo's etc.) using Lipofectin reagent per the manufacture's protocol (Gibco):

S-MIF: 5'-GCC-ATC-ATG-CCG-ATG-TTC-AT-3' [SEQ ID NO. 1] (SENSE, HUMAN MIF)
AS-MIF: 5'-ATG-AAC-ATC-GGC-ATG-ATG-GC-3' [SEQ ID NO. 2] (ANTI-SENSE, HUMAN MIF)

After 16 hours incubation under standard cell culture conditions (37° C. 5% CO in humidified air atmosphere) the proliferative activity of these cultures was measured over the subsequent eight hours by the incorporation of [$^3$H] thymidine (4 µCi/ml; DuPont) into DNA as measured by liquid scintillation counting.

Relative to sense MIF constructs, anti-sense MIF mRNA inhibited K562 cell proliferation by about 50% (FIG. 6). The results demonstrate that the direct anti-proliferative effect of anti-MIF treatment on tumor cells, and more specifically the activity of MIF-specific antisense treatment against leukemia cell proliferation.

10. INHIBITION OF LYMPHOMA VASCULARIZATION IN VIVO BY TREATMENT WITH NEUTRALIZING ANTI-MIF MONOCLONAL ANTIBODIES

To further characterize the nature of the anti-tumor activity of anti-MIf antibodies administered in vivo, tumor neovascularization was assessed by immunohistochemical staining for a constitutively expressed endothelial cell surface marker (CD31, also known as platelet endothelial cell adhesion molecule or PECAM-1). Tumor growth was initiated in normal mice by transplantation of syngeneic lymphoma cells. Tumor cell-inoculated mice were treated from the time of tumor cell transfer either with anti-MIF or control antibodies and tumor vascularization, as visualized in histological specimens of harvested tumors by immunohistochemical staining specific for CD31, was compared between sections from anti-MIF versus control antibody-treated tumor-bearing mice.

B cell lymphoma cells (38C13 cell line; provided by J. D. Kemp, Dept. of Pathology, U. of IA) were collected from exponential growth phase culture (RPMI/10% FBS), centrifuged 10 min at 30×g, washed twice with PBS, and adjusted to 1×10$^6$ cells/ml (in PBS). Following the methods of Kemp et al. (1), groups of five C3H/HeN female mice (20–25 g; Harlan Labs, NY) were shaved on the upper flank and 0.05 ml of the 1×10$^6$/ml 38C13 cell suspension (5×10$^4$ cells) was injectedi.d. with a 1-ml syringe and 27-guage needle. Within 30 min, mice received a 0.2 ml (0.3 mg) i.p. injection of either on $IgG_1$ isotype control antibody (Pharmingen; San Diego, Calif.) or anti-MIF monoclonal antibody (XIV.15.5, $IgG_1$ subclass mAb provided by C. Metz, Dept. of Med. Biochemistry, The Picower Institute). Antibody injections were repeated every 48 hours for 6 days. Mice were euthanized by $CO_2$ asphyxiation and tumors were excised, fixed in buffered neutral 10% formalin, sectioned, and processed for immunohistochemical analysis. After quenching endogenous peroxidases with $H_2O_2$ (3%), the deparaffinized sections were incubated sequentially with an anti CD31 mAb (1:50 dilution; clone MEC 13.3; Pharmingen; San Diego, Calif.) or an $IgG_2$ isotype control antibody (Pharmingen), with an alkaline phosphatase-linked anti-mouse IgG secondary antibody, and developed with new fuchsin (DAKO) as substrate. Control sections stained with an isotype control or without primary antibody showed no immunoreactivity.

As revealed by immunohistochemical staining for the endothelial cell marker, CD31, sections of tumor tissue harvested from mice treated with control antibody show a uniformly dense bed of neo-vascularization. Sections of tumor tissue from mice treated with a mouse anti-MIF monoclonal antibody, however, show immunohistochemical evidence of only sparse vascularization of the tumor mass. The tumors that developed in animals treated with anti-MIF mAbs were significantly smaller than the tumors that developed in the control Ab treated mice masses than the tumors in control antibody-treated mice.

A comparison of the mean number of CD31-positive capillary profiles per high-power field (400×) in immuno-histochemically stained sections of tumors harvested from anti-MIF mAb-treated versus control Ab-treated animals were made. The number of CD31+ capillary profiles was tabulated for five high power fields of histology sections of tumor samples taken from two animals from each group (anti-MIF versus control antibody-treated). These tumors were those harvested as described in the initial tumor outgrowth experiments of Example 6, FIGS. 1 and 2. The results of this comparison of the degree of vascularization are shown in FIG. 7, which clearly demonstrates that the tumors growingin anti-MIF antibody-treated animals, in addition to being smaller than those occurring in control antibody-treated animals, are significantly less vascularized on a per unit volume basis. Thus the anti-tumor benefits of therapeutic agents and methods directed against MIF is shown to occur, at least in part, through an apparent effect on host-dependent processes, such as angiogenesis, that contribute powerfully to determining the course of tumor development.

The present invention is not to be limited in scope by the specific embodiments described which are intended as single illustrations of individual aspects of the invention, and functionally equivalent methods and components are within the scope of the invention. Indeed various modifications of the invention, in addition to those shown as described herein will become apparent to those skilled in the art from the foregoing description and accompanying drawings. Such modifications are intended to fall within the scope of the appended claims.

A number of references have been cited and the entire disclosures of which are incorporated herein by reference.

11. DEPOSIT OF MICROORGANISMS

Murine hybridomas strains III.D.9 and XIV.15.5 were deposited on Oct. 24, 1996, with the American Type Culture Collection, 1201 Parklawn Drive, Rockville, Md. 20852, under the provisions of the Budapest Treaty on the International Recognition of the Deposit of Microorganisms for the Purposes of Patent Procedures.

What is claimed is:

1. An antisense molecule that is complementary to MIF mRNA and consists of the following nucleotide sequence:

5' ATG AAC ATC GGC ATG ATG GC 3' [SEQ ID NO: 2].

* * * * *

UNITED STATES PATENT AND TRADEMARK OFFICE
CERTIFICATE OF CORRECTION

PATENT NO.      : 6,774,227 B1
DATED           : August 10, 2004
INVENTOR(S)     : Richard J. Bucala et al.

It is certified that error appears in the above-identified patent and that said Letters Patent is hereby corrected as shown below:

<u>Title page,</u>
Item [56], References Cited, OTHER PUBLICATIONS, "Gewirtz et al.," reference, "Apr. 1998.*" should read -- Apr. 1996.* --.

<u>Column 2,</u>
Line 50, "A38C13" should read -- A 38C13 --.

<u>Column 3,</u>
Line 61, "(37° C.," should read -- (37°C, --.

<u>Column 9,</u>
Line 24, "22° C." should read -- 22°C --

<u>Column 11,</u>
Line 42, "tumorgenesis." should read -- tumorigenesis --.

<u>Column 13,</u>
Line 13, "Elisa" should read -- ELISA --.
Line 36, "4° C." should read -- 4°C --.

<u>Column 15,</u>
Line 23, "bernign-" should read -- benign --.
Lines 28-29, "Adminiatration" should read -- Administration --.
Line 46, "addition." should read -- edition. --.

<u>Column 17,</u>
Line 46, "Various of sustained-release" should read -- Various sustained-release --.
Line 54, "gel-phase" should read -- gel- phase --.

<u>Column 19,</u>
Line 3, "Packing" should read -- Packaging --.
Line 52, "we" should read -- were --.
Line 56, "we" should read -- were --.

UNITED STATES PATENT AND TRADEMARK OFFICE
CERTIFICATE OF CORRECTION

PATENT NO. : 6,774,227 B1
DATED : August 10, 2004
INVENTOR(S) : Richard J. Bucala et al.

It is certified that error appears in the above-identified patent and that said Letters Patent is hereby corrected as shown below:

Column 20,
Line 51, "(45.6±4.6" should read -- (45.6 ± 4.6 --; and "46.1±3.4 should read -- 46.1 ± 3.4 --.
Line 53, "mean±sd)." should read -- mean ± sd) --.
Line 54, "mc)re" should read -- more --.
Line 55, "(246.7±41,4" should read -- (246.7 ± 41.4 --.
Line 56, "97.2±12.2," should read -- 97.2 ± 12.2, --.
Line 57, "tot eh" should read -- to the --.

Column 22,
Line 2, "(37° C." should read -- (37°C --.
Line 20, "anti-MIf" should read -- anti-MIF --.
Line 40, "injectedi.d." should read -- injected i.d. --; and "guage" should read -- gauge --.
Line 42, "on" should read -- an --.

Column 23,
Line 12, "growingin" should read -- growing in --.

Column 24,
Line 17, insert after "Purposes of Patent Procedures":--, and assigned accession numbers HB-12220 and HB-12221, respectively. --.

Signed and Sealed this

Sixteenth Day of November, 2004

JON W. DUDAS
*Director of the United States Patent and Trademark Office*

```
SEQUENCE LISTING

<160> NUMBER OF SEQ ID NOS: 3

<210> SEQ ID NO 1
<211> LENGTH: 20
<212> TYPE: DNA
<213> ORGANISM: Homo sapiens

<400> SEQUENCE: 1
gccatcatgc cgatgttcat                                                   20

<210> SEQ ID NO 2
<211> LENGTH: 20
<212> TYPE: DNA
<213> ORGANISM: Homo sapiens

<400> SEQUENCE: 2
atgaacatcg gcatgatggc                                                   20

<210> SEQ ID NO 3
<211> LENGTH: 348
<212> TYPE: DNA
<213> ORGANISM: Homo sapiens

<400> SEQUENCE: 3
atgccgatgt tcatcgtaaa caccaacgtg ccccgcgcct ccgtgccgga cgggttcctc        60
tccgagctca cccagcagct ggcgcaggcc accggcaagc cccccagta catcgcggtg        120 cacgtggtcc cggaccagct catggccttc ggcggctcca gcgagccgtg cgcgctctgc      180
agcctgcaca gcatcggcaa gatcggcggc gcgcagaacc gctcctacag caagctgctg      240
tgcggcctgc tggccgagcg cctgcgcatc agcccggaca gggtctacat caactattac      300
gacatgaacg cggccagtgt gggctggaac aactccacct tcgcctaa                    348
```